US00PP29961P3

(12) United States Plant Patent
Goffreda et al.

(10) Patent No.: US PP29,961 P3
(45) Date of Patent: Dec. 11, 2018

(54) PEACH TREE NAMED 'NJ359'

(50) Latin Name: ***Prunus persica* L.**
Varietal Denomination: NJ359

(71) Applicant: RUTGERS, THE STATE UNIVERSITY OF NEW JERSEY, New Brunswick, NJ (US)

(72) Inventors: Joseph C. Goffreda, Millstone Township, NJ (US); Anna M. Voordeckers, East Windsor Township, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 67 days.

(21) Appl. No.: 15/530,541

(22) Filed: Jan. 26, 2017

(65) Prior Publication Data

US 2018/0213694 P1 Jul. 26, 2018

(51) Int. Cl.
*A01H 5/08* (2018.01)
*A01H 6/74* (2018.01)

(52) U.S. Cl.
USPC ..... Plt./198
CPC ..... *A01H 6/7463* (2018.05)

(58) Field of Classification Search
USPC ..... Plt./156, 180, 194, 198
See application file for complete search history.

(56) References Cited

PUBLICATIONS

Callahan Michigan Show Peach and Plum Great Lakes Expo, Plums, Pluots, Flat Peach, and Other Novel Stone Fruits Nov. 22, 2016, retrieved on May 1, 2018, retrieved from the Internet at www.glexpo.com/summaries/2016summaries/Peach-Plum.pdf, 13 pp. (Year: 2016).*

* cited by examiner

*Primary Examiner* — Susan McCormick Ewoldt
*Assistant Examiner* — Karen M Redden
(74) *Attorney, Agent, or Firm* — Patrick J. Daugherty; Daugherty & Del Zoppo Co., L.P.A.

(57) ABSTRACT

A new and distinct peach variety of *Prunus persica* named 'NJ359' is provided. This variety is distinguished from other peach varieties by its unique combination of non-showy flowers, large, nearly round, freestone fruit that have very good eating quality due to their aromatic, sweet, and moderately acidic flavor, and are generally well colored for a peach that ripens in late season.

6 Drawing Sheets

Latin name of genus and species of the plant claimed: *Prunus persica* L.

Variety denomination: 'NJ359'.

CROSS REFERENCE TO RELATED APPLICATIONS

NONE

STATEMENT REGARDING FEDERALLY SPONSORED RESEARCH OR DEVELOPMENT

NONE

BACKGROUND OF THE INVENTION

The present invention relates to a new and distinct variety of peach tree named 'NJ359'. Our new tree resulted from crossing 'Flameprince' (non-patented) as the seed parent with our proprietary peach seedling selection 'NJ260' (U.S. Plant Pat. No. 4,572) as the pollen parent. The new variety differs from seed parent 'Flameprince' in that the new variety produces slightly larger fruit and that has better flavor and aromatics. The new variety differs from pollen parent 'NJ260' in that the new variety produces more attractive fruit that have superior eating quality. The resulting tree was selected when growing in a cultivated area as the 76$^{th}$ tree in the 65$^{th}$ row of Block K at a fruit research farm in Cream Ridge, N.J.

BRIEF SUMMARY OF THE INVENTION

'NJ359' differs from the related cultivar 'Autumnglo' (unpatented), in that 'NJ359' fruit are slightly larger than the fruit of 'Autumnglo' and the trees of 'NJ359' are slightly more tolerant of bacterial leaf spot (*Xanthomonas campestris* pv. *pruni*) than 'Autumnglo'. The 'NJ359' variety is also distinguished from other peach varieties due to the following unique combination of characteristics:

- Trees produce large, yellow-orange fleshed fruit, with an attractive red blush and red-purple mottle over a bright yellow-orange ground color.
- Excellent production of firm fruit that ripen in late season.
- Fruit have very good eating quality due to their aromatic, sweet, and moderately acidic flavor.

The variety was asexually reproduced at a fruit research farm in Cream Ridge, N.J. Asexual reproduction of this new variety by budding onto 'Bailey' peach seedling rootstock (non-patented) shows that the foregoing characteristics are so reproduced.

The following detailed description concerns the original tree, 'NJ359'. The original tree and asexual progeny have been observed growing in a cultivated area at the fruit research farm in Cream Ridge, N.J. Certain characteristics of this variety, such as growth and color, may change with changing environmental conditions (such as, light, temperature, moisture, nutrient availability) or other factors. Color descriptions and other terminology are used in accordance with their ordinary dictionary descriptions, unless the context clearly indicates otherwise. Color designations are made with reference to *The Royal Horticultural Society* (*R.H.S.*) *Colour Chart* (1966)

BRIEF DESCRIPTION OF THE DRAWINGS

This new variety is illustrated by the accompanying photographic drawings, depicting the peach tree plant at an approximate age of five (5) years old by the best possible color representation using color photography. Colors are approximate as color depends on horticultural practices, such as light level, fertilization rate, and other conditions and, therefore, the color characteristics of this new variety should be determined with reference to the observations described herein, rather than from these illustrations alone.

Figure 1:
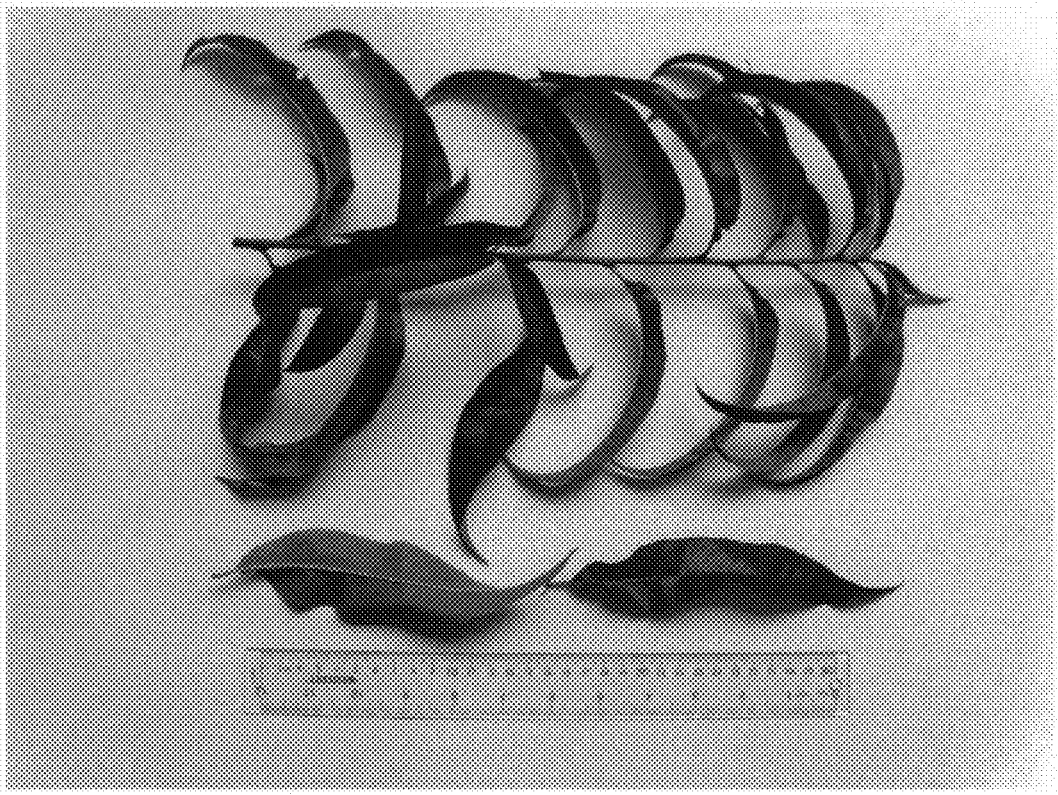
FIG. 1 is a color photograph taken on Aug. 22, 2014 of a characteristic twig of 'NJ359' in late spring bearing typical leaves of the foliage.
Figure 2:
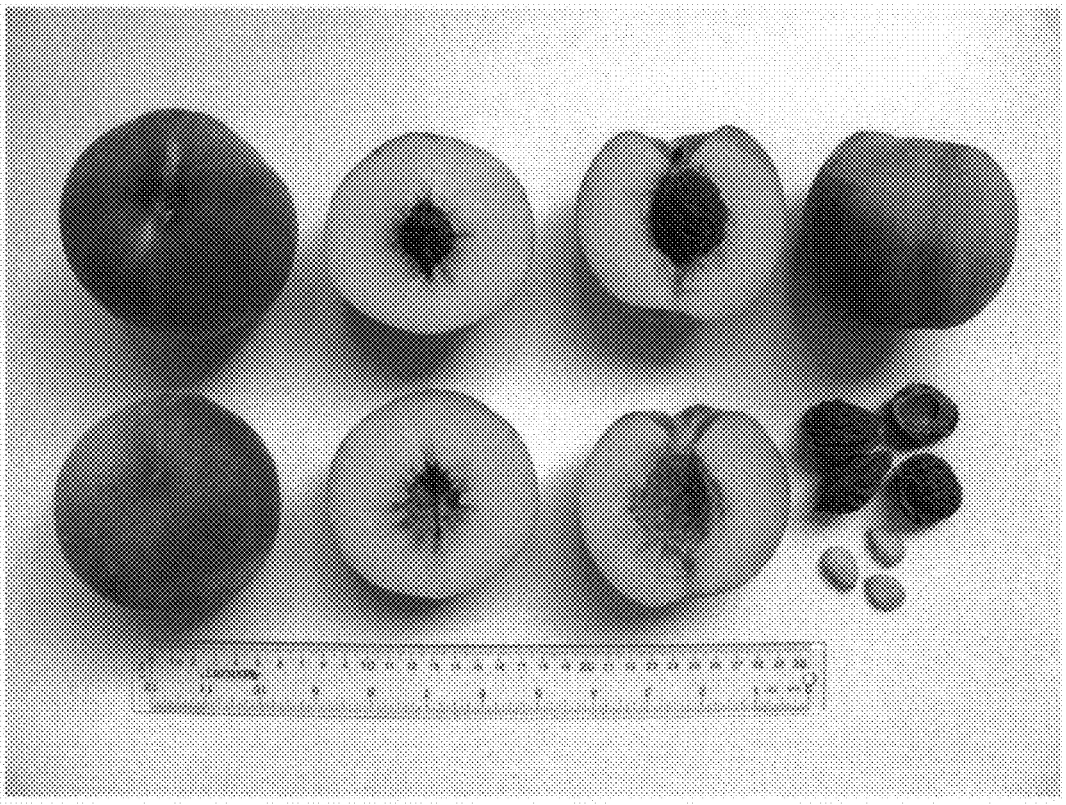
FIG. 2 is a color photograph taken on Sep. 2, 2014 of characteristic mature fruit and stones of 'NJ359'. Whole fruit are presented in three positions and both a transverse and longitudinal cross section to illustrate that the pericarp does not adhere to the pit when the fruit is mature. The stones exemplify the obovate shape and pits and grooves on the surface of the stone.
Figure 3:
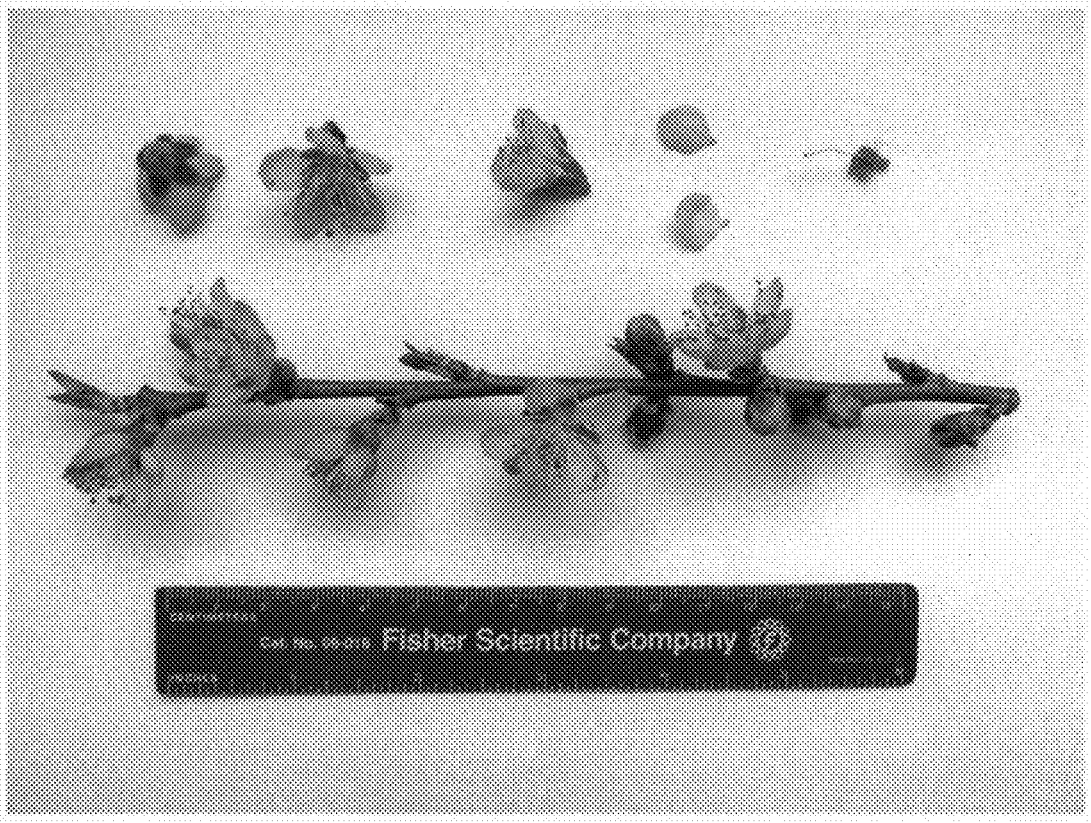
FIG. 3 is a color photograph of a characteristic twig that illustrates the typical flower buds and small, non-showy flowers of 'NJ359' observed on a tree at the fruit research farm in Cream Ridge, N.J. on Apr. 21, 2015.
Figure 4:
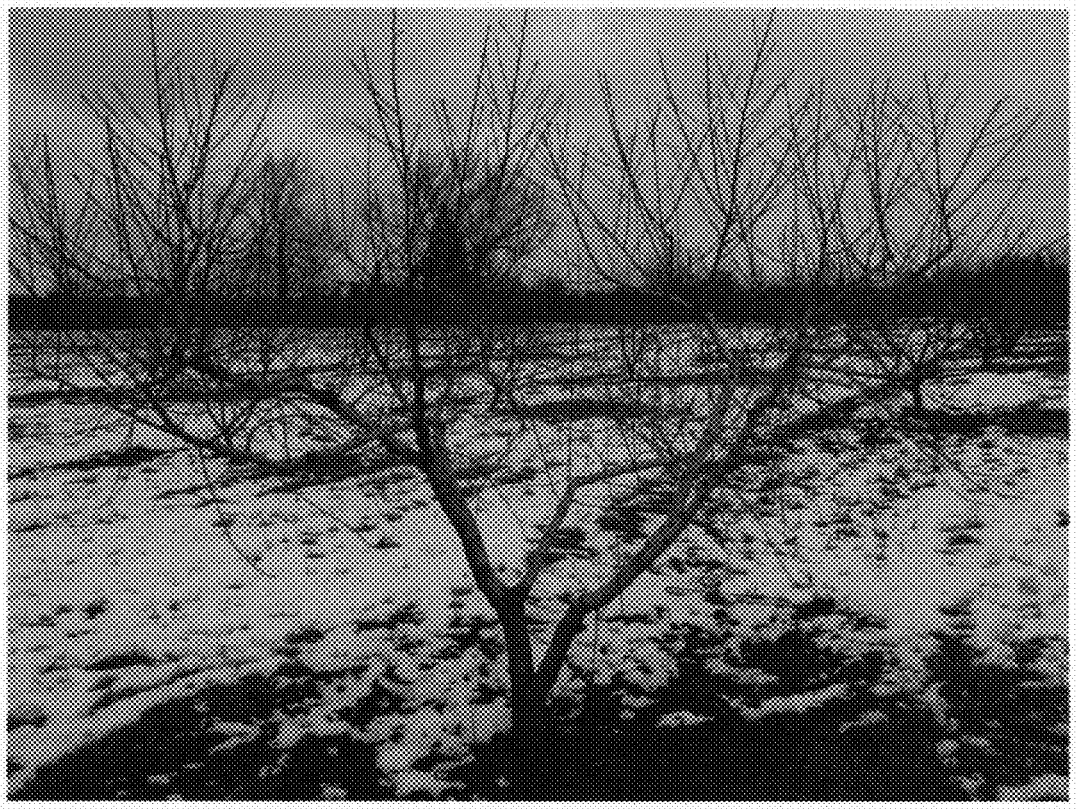
FIG. 4 is a color photograph of a dormant tree of 'NJ359', prior to pruning, in late winter that illustrates the spreading growth habit of a tree at said fruit research farm in Cream Ridge, N.J. on Feb. 8, 2016.
Figure 5:
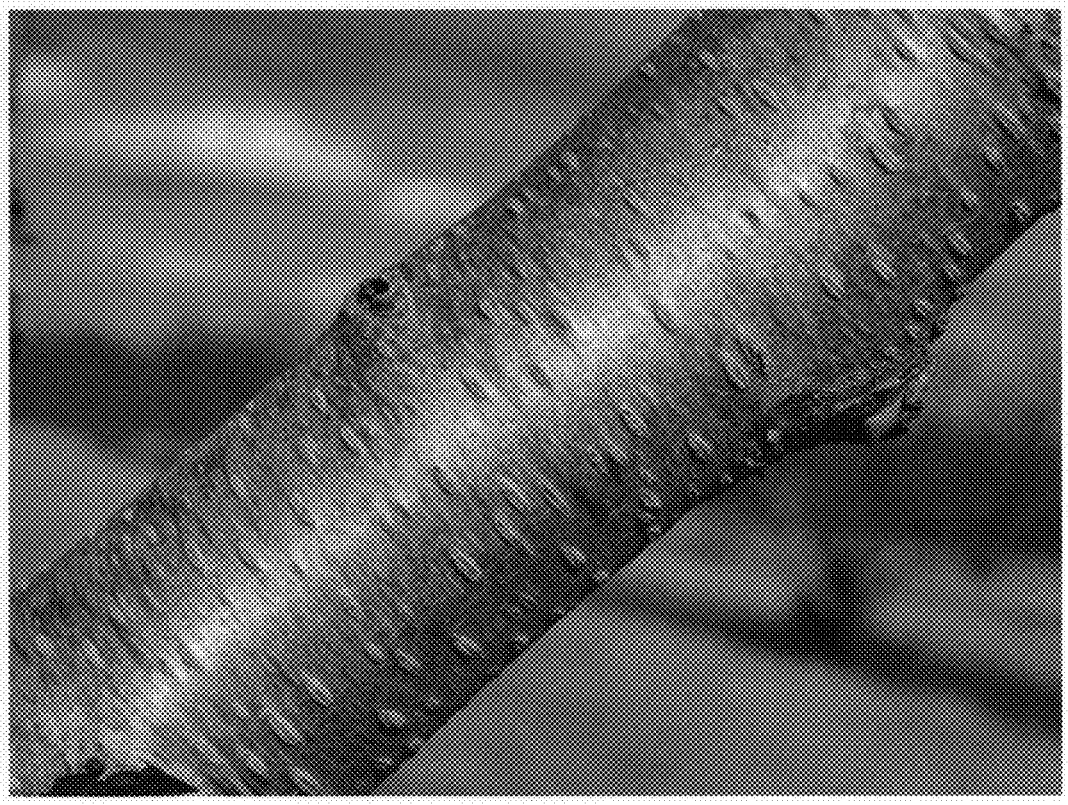
FIG. 5 is a color photograph taken on Mar. 17, 2015 of immature bark of 'NJ359' that illustrates color and the high density of conspicuous elliptic lenticels on the immature bark.
Figure 6:
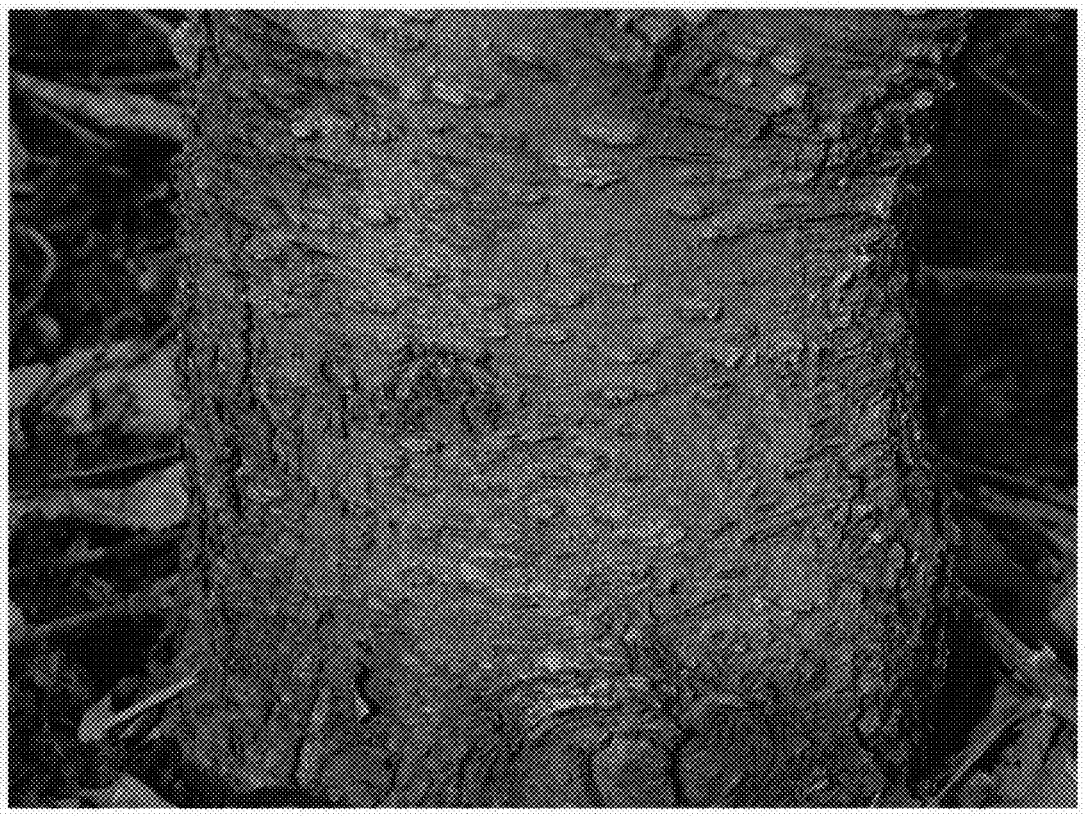
FIG. 6 is a color photograph taken on Mar. 11, 2015 of mature bark of 'NJ359' that illustrates the grey color, moderately rough texture and prominent, large lenticels of the mature bark.

The colors of and illustration of this type may vary with lighting and other conditions under which conditions and, therefore, color characteristics of this new variety should be determined with reference to the observations described herein, rather than from these illustrations alone.

DETAILED BOTANICAL DESCRIPTION

The following detailed description of the 'NJ359' variety is based on observations of an asexually reproduced tree. The observed tree was five years of age and growing on 'Bailey' seedling rootstock (non-patented) at the fruit research farm in Cream Ridge, N.J.

Scientific name: *Prunus persica* L.

Parentage:

*Seed parent*.—'Flameprince'.

*Pollen parent*.—'NJ260' (Expired U.S. Plant Pat. No. 4,572).

Tree:

*Vigor*.—Vigorous.

*Plant hardiness zone*.—Growth of plants has only been observed in zone 6b.

*Dormant flower bud cold tolerance*.—At least to −21° C.

*Leaf bud burst*.—Typically in mid-April when grown in Cream Ridge, N.J., but can vary by one to two weeks.

*Overall shape*.—Spreading.

*Height*.—Average as compared to other peach cultivars. For example, measurement of a typical grafted tree on 'Bailey' peach seedling rootstock (non-patented) at five years after planting shows an average height of 2.7 meters when grown in Cream Ridge, N.J.

*Width*.—Average as compared to other peach cultivars. For example, measurement of a typical grafted tree on 'Bailey' peach seedling rootstock (non-patented) at five years after planting shows an average width of 4.0 meters when grown in Cream Ridge, N.J.

*Caliper*.—Five year old tree is 37 cm. in circumference measured at 20 cm. from the ground.

Trunk and branches:

*Trunk bark texture*.—Moderately rough with prominent, large lenticels.

*Trunk bark color*.—Grey (between RHS 201C and RHS 201D).

*Primary branches*.—Branches that are approximately 15 cm. in circumference are greyed-orange (RHS 176B) overlaid with grey (RHS 201D). Lenticels: High density, approximately 1.6 per square cm; elliptical in shape and conspicuous; typical examples of which averaged 4.4 mm. in length and 2.1 mm. in width; perimeter color is greyed-green (between RHS 198C and RHS 198D) becoming greyed-orange (between RHS 164C and RHS 164D) towards the center. Branch pubescence: None. New growth bark: Greyed-purple (RHS 183B) in sun; greyed-purple (RHS 182B) over a yellow-green (RHS 152D) ground color in shade.

*Internodes*.—Length averaging 19.2 mm. on a one-year shoot.

Leaves:

*Texture*.—Glabrous, both surfaces.

*Sheen*.—Young leaves semi-glossy with a flat finish on the underside.

*Length*.—About 158 mm. to 199 mm, averaging about 175 mm. including the petiole.

*Width*.—About 32 mm. to 43 mm., averaging about 37 mm.

*Petiole*.—Averaging 11.2 mm. long and about 2.0 mm. in diameter. Color: yellow-green (146 C).

*Margin*.—Crenate.

*Margin undulation*.—Margins generally entire; occasionally may have broad undulations.

*Form*.—Lanceolate, and concave in cross section.

*Apex*.—Sharply acuminate, typically sharply curved downward.

*Base*.—Acute.

*Venation*.—Pinnate.

*Glands*.—Number: About 3 to 5, averaging about 4. Position: Located on the petiole and leaf margin near the base. Size: Length averaging 1.7 mm. and width averaging 0.9 mm. Form: Reniform.

*Stipules*.—Stipules are present on immature leaves, but they are not persistent. Typically, there are two per immature leaf, with an average length of 11.7 mm. The color is yellow-green (RHS 146 B), becoming yellow-green (152 A) just prior to dehiscence. None observed on mature leaves.

*Leaf color*.—Upper leaf surface: Yellow-green (RHS 146A). Lower leaf surface: Yellow-green (RHS 148B). Vein: Yellow-green (RHS 151D).

*Pubescence*.—None.

Flowers:

*Size*.—Non-showy, small size, typical flower measuring between 20 mm. to 26 mm., averaging about 22 mm. across.

*Color*.—Dormant bud: Grey (RHS 201D). Pink stage bud: Red-purple (between RHS 62A and RHS 62B). Open flower: Freshly opened flowers are red (RHS 56C) becoming red (RHS 55C) at the petal's margins.

*Petals*.—Typically five petals per flower; slightly cupped, medium elliptic, margin entire, averaging about 11.9 mm. long and 10.0 mm. wide. Upper and lower petal color is red (RHS 56C) becoming fringed with red (RHS 55C) at the petal's margins.

*Petal apex*.—Obtuse.

*Petal base*.—Cuneate at point of attachment.

*Stamens*.—Position: Perigynous and near the point of attachment of the petals. Number: Variable, typical range 38 and 50, averaging 42.3. Length: Variable, between 9.0 mm. to 12.9 mm., averaging 11.1 mm. Filament color: White (RHS 155A). Anther color: Red (RHS 44c).

*Pistil*.—Number: One. Size: Length between 17 and 19 mm., averaging 18 mm. Pistil color: Yellow-green (RHS 145B). Ovary: Moderate, medium length pubescence and ellipsoid in shape, color yellow-green (RHS 145A).

*Stigma*.—Located at approximately the same level as the majority of the stamens.

*Sepals*.—Number: Five. Pubescence: Length short, low density. Color: Greyed-purple (RHS 183D). Shape: Triangular, with a rounded apex. Size: Length averaging 6.1 mm., width averaging 4.5 mm.

*Nectar cup color*.—Greyed-orange (RHS 168B).

*Pollen*.—Viable and abundant, typically self-fruitful; yellow (RHS 11A) in color.

*Fragrance*.—Very slight.

*Bloom season*.—Onset of bloom in 2014 on April 17; full bloom on April 23.

Fruit:

*Size*.—Large, averaging about 7.7 cm. long, 8.1 cm. wide parallel to the suture and 8.3 cm. wide perpendicular to the suture.

*Typical weight*.—274 g.

*Form*.—Longitudinal section: Nearly round, some fruit may have unequal halves. Traverse section: Nearly round, some fruit may be slightly triangular.

*Suture*.—Shallow, extending from base to apex.

*Ventral surface*.—Nearly smooth at its base, becoming lipped towards the apex.

*Base*.—Flat.

*Apex*.—Flat; apex tip is a small point.

*Stem*.—Average length of 7 mm. and an average diameter 4.0 mm.

*Skin*.—Thickness: Medium. Flesh Firmness: Above average. Surface: Pubescent, generally light and short. Tenacity: Medium. Astringency: None. Tendency to crack: Low. Color: Blush is red (RHS 46B); mottle and stripes are red-purple (between RHS 59A and RHS 59B); ground color is yellow-orange (RHS 16C).

*Fruit properties*.—Flesh color: Yellow-orange (RHS 14C); red (RHS 46C) adjacent to stone. Flesh adhesion: Freestone. Juice: Moderate. Texture: Firm, but melting. Fibers: Not noticeable. Ripens: Between August 28 and September 8 at Cream Ridge, N.J. Flavor: Sweet, moderate acidity. Soluble solids: 13.5%. Aroma: Moderate. Eating quality: Good to very good.

*Keeping quality*.—Medium. Has held its flavor and firmness for at least 14 days in cold storage at 1° C. to 2° C.

*Shipping quality*.—Good. No bruising or scaring disorders have been observed.

*Usage*.—Dessert.

*Market*.—Local and long distance.

*Productivity*.—Very good. Peach productivity varies greatly depending upon conditions inclusive of winter and spring temperatures, rainfall, tree density, pruning methods, soil type, fertilization, irrigation, and degree of fruit thinning. Trees have produced a full crop in 7 out of 10 and at least a partial crop 9 out of 10 years in Cream Ridge, N.J.

Stone:

*Type*.—Freestone.

*Form*.—Obovate.

*Base*.—Narrow.

*Apex*.—Wide.

*Surface*.—Pits and grooves.

*Ventral suture*.—Large.

*Dorsal ridge*.—Medium height, narrow width, forming medium depth lines.

*External color*.—Greyed-orange (RHS 166D) overlaid with greyed purple (RHS 183).

*Cavity surface color*.—Greyed-orange (between RHS 165c and RHS 165D).

*Average stone dry weight*.—9.9 g.

*Average stone wall thickness*.—Varies between 6.0 mm. along the dorsal ridge to 9.9 mm. at the base.

*Size*.—Averages about 40.2 mm. long, 30.2 mm. wide parallel to the dorsal ridge, and 40.2 mm. wide perpendicular to the dorsal ridge.

*Tendency to split*.—Typically low when well cropped.

Kernel:

*Form*.—Elliptic to slightly obovate.

*Skin color*.—Greyed-orange (RHS 164B).

*Vein color*.—Greyed-orange (RHS 164A).

*Viability*.—Yes.

*Size*.—Averages about 19.1 mm. long, 11.8 mm. wide, and 3.9 mm. in breadth.

Plant/fruit disease and pest resistance/susceptibility: No atypical resistances/susceptibilities have been noted under normal cultural practices.

We claim:

1. A new and distinct variety of peach tree, substantially as herein shown and described.

* * * * *